(12) United States Patent
Boussignac

(10) Patent No.: US 6,467,482 B1
(45) Date of Patent: Oct. 22, 2002

(54) RESPIRATORY ASSISTANCE APPARATUS

(76) Inventor: Georges Boussignac, 1, Avenue de Provence, 92160 Antony (FR)

(*) Notice: Subject to any disclaimer, the term of this patent is extended or adjusted under 35 U.S.C. 154(b) by 0 days.

(21) Appl. No.: 09/503,114

(22) Filed: Feb. 14, 2000

(51) Int. Cl.[7] .............................................. A62B 18/08
(52) U.S. Cl. ............................ 128/206.24; 128/206.26; 128/207.14; 128/207.18
(58) Field of Search ....................... 128/206.24, 206.26, 128/207.14, 207.18

(56) References Cited

U.S. PATENT DOCUMENTS

| | | | | |
|---|---|---|---|---|
| 4,799,477 A | * | 1/1989 | Lewis .................... | 128/200.27 |
| 4,811,730 A | * | 3/1989 | Milano ................... | 128/202.28 |
| 4,834,085 A | * | 5/1989 | Webster, II ............ | 128/202.29 |
| 4,971,051 A | | 11/1990 | Toffolon | |
| 5,139,510 A | | 8/1992 | Goldsmith, III et al. | |
| 5,269,296 A | | 12/1993 | Landis | |
| 5,355,878 A | * | 10/1994 | Griffiths et al. ........ | 128/201.23 |
| 5,392,774 A | * | 2/1995 | Sato ....................... | 128/207.14 |
| 5,452,715 A | * | 9/1995 | Boussignac ............ | 128/207.14 |
| 5,469,842 A | * | 11/1995 | Flynn ..................... | 128/202.28 |
| 5,738,094 A | * | 4/1998 | Hoftman ................ | 128/206.24 |
| 5,803,076 A | * | 9/1998 | Myers .................... | 128/205.25 |
| 5,975,079 A | * | 11/1999 | Hellings et al. ........ | 128/206.21 |

FOREIGN PATENT DOCUMENTS

EP 0747078 12/1996

* cited by examiner

Primary Examiner—Dennis Ruhl
Assistant Examiner—Michael Mendoza
(74) Attorney, Agent, or Firm—Stevens, Davis, Miller & Mosher, LLP

(57) ABSTRACT

According to the invention, the respiratory assistance apparatus comprising a chamber (3), provided with a respiratory-gas inlet and a respiratory-gas outlet, and an inflatable flexible bladder (11), intended to bear sealingly on a part (9) of a patient, is noteworthy:

in that it includes an inflatable flexible envelope (12) which surrounds said bladder (11); and in that the wall thickness of said envelope (12) is less than that of said inflatable bladder (11) in order to give said envelope a greater flexibility than the flexibility of the latter.

12 Claims, 2 Drawing Sheets

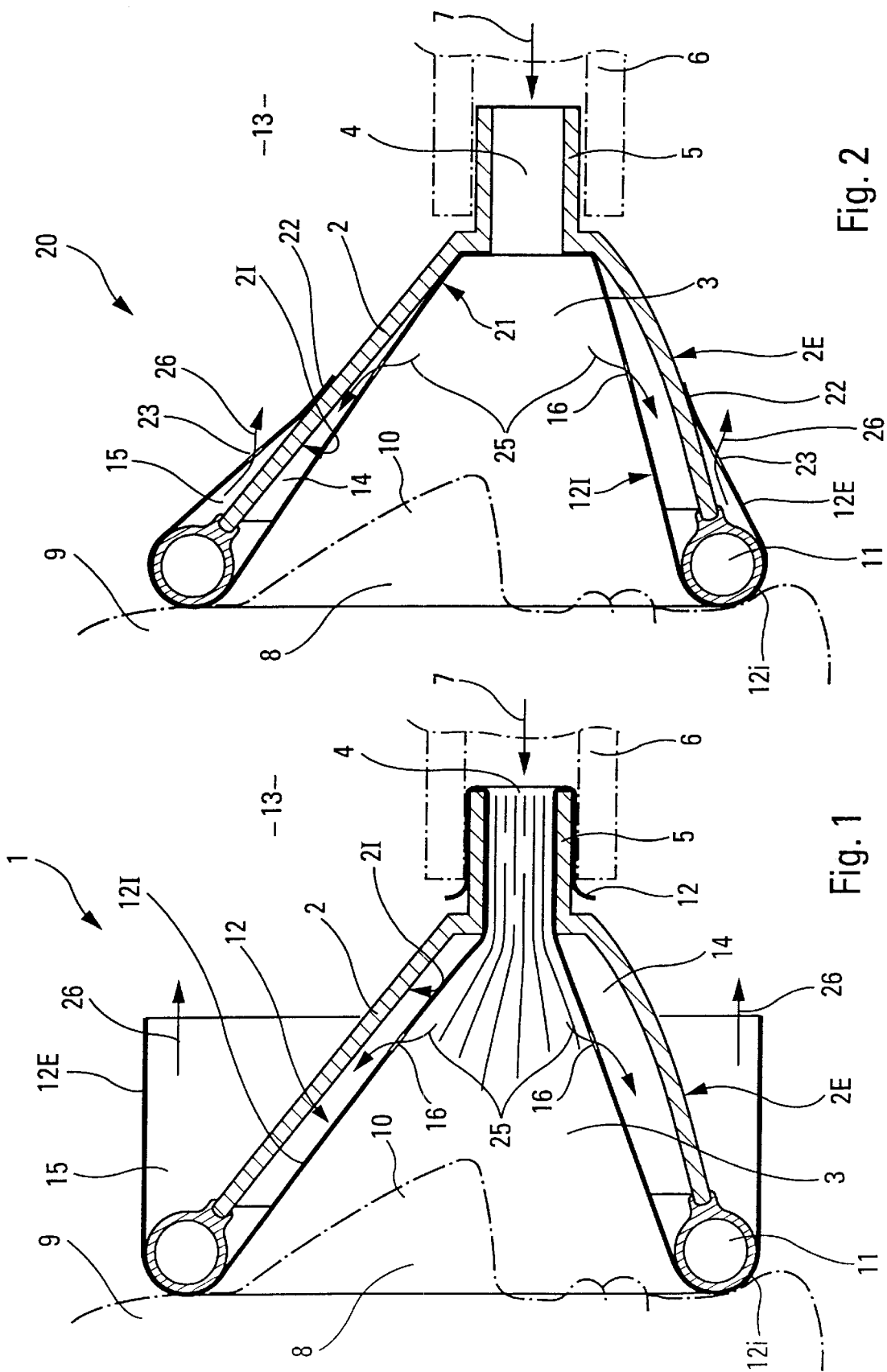

RESPIRATORY ASSISTANCE APPARATUS

FIELD OF THE INVENTION

The subject of the present invention is a respiratory assistance apparatus that can be used on patients whose spontaneous respiration is absent or insufficient.

DESCRIPTION OF THE RELATED ART

Respiratory assistance apparatuses are already known which make it possible for a respiratory gas coming from an external source to be taken into the lungs of a patient, said apparatuses comprising:

a chamber provided with a respiratory-gas inlet intended to be connected to said source and with a respiratory-gas outlet intended to be connected to an airway of said patient; and an inflatable flexible bladder intended to bear on a part of said patient in order to seal between said respiratory-gas outlet and the outside.

Such known respiratory assistance apparatuses may, for example, take the form:

of a respiratory mask, said chamber of which is bounded by a hollow shell intended to be applied, by its opening which constitutes said gas outlet, to the face of the patient, enclosing the nose of the latter. The respiratory-gas inlet is then formed by an endpiece integral with the bottom of said shell, while said inflatable bladder has the shape of a bead going around the outline of the opening of said shell and interposed between said opening and the patient's face; or else of a nasal intubation device, said chamber of which is bounded by a tubular element intended to be inserted into a nostril of the patient. In this case, said respiratory-gas inlet and outlet are formed by the opposite ends of said tubular element and said inflatable bladder is in the form of a balloon carried by the external wall of said tubular element and interposed between the latter and the internal wall of the nostril.

Whatever the embodiments of these known respiratory assistance apparatuses, they have the drawback that their inflatable bladder cannot seal satisfactorily. This is because, in order to be able to withstand the inflation pressure, said flexible bladder must have a relatively thick wall which gives it a certain rigidity and consequently prevents it from exactly matching the irregularities in the relief of that part of said patient (the face or internal nostril wall, for example) to which it is applied. This therefore results in leakage, entailing expensive loss of respiratory gas. In addition, in the case of a mask, the respiratory gas passing between the bead and the patient's face, as a result of the deficiencies in sealing by said bead, penetrates the patient's eyes and is the cause of ocular irritations and of conjunctivitis.

In order to compensate for such sealing deficiencies, practitioners are forced:

to increase the pressure with which said inflatable flexible bladder is applied to the corresponding part of the patient. Such an increase in application pressure is obtained either by forcibly applying the mask to the face (using elastic straps passing behind the head for example) or by increasing the internal pressure of the balloon of the nasal intubation device. However, a high bladder application pressure results in the formation of sores at the places where the respiratory apparatus is applied to the patient; and/or to increase the pressure to which the respiratory gas is taken into the respiratory apparatus. In this case, the mucous membranes reached by the respiratory gas may as a result be injured by this gas. In addition, in the latter case, gas leaks still occur—and are even exacerbated—with their drawbacks.

SUMMARY OF THE INVENTION

The object o the invention is to remedy these drawbacks and relates to a respiratory assistance apparatus of the type indicated above, by virtue of which any risk of leakage of respiratory gas, at the inflatable bladder of said apparatus, may be avoided.

For this purpose, according to the invention, the respiratory assistance apparatus making it possible for a respiratory gas coming from an external source to be taken into the lungs of a patient, said apparatus comprising:

a chamber provided with a respiratory-gas inlet intended to be connected to said source and with a respiratory-gas outlet intended to be connected to an airway of said patient; and a thin-wall inflatable flexible bladder intended to bear on a part of said patient in order to seal between said respiratory-gas outlet and the outside, is noteworthy:

in that it includes an inflatable flexible envelope surrounding said inflatable flexible bladder; and in that the wall thickness of said envelope is less than that of said inflatable bladder in order to give said envelope a greater flexibility than the flexibility of the latter.

Thus, when said inflatable flexible bladder cannot be sealingly applied against said bearing part of the patient, the space which results therefrom is closed off by said inflated flexible envelope, which thus ensures application sealing at the places where this sealing cannot be obtained by said inflatable bladder.

Preferably, said flexible envelope is made of a plastic film a few microns in thickness.

Said inflatable flexible envelope may be inflated in an appropriate manner either using a source of auxiliary pressure or using said external respiratory-gas source.

In one advantageous embodiment, said flexible envelope communicates, on one side of the bladder, with said chamber and, on the other side of said bladder, with the outside. Thus, said flexible envelope is therefore inflated by the pressurized respiratory gas coming from said chamber and being discharged to the outside.

If said respiratory assistance apparatus has the shape of a mask, said chamber of which is defined by a hollow shell intended to be applied, by its opening which constitutes said gas outlet, to the face of a patient, enclosing the latter's nose, the respiratory-gas inlet being provided in the bottom of said shell and said inflatable bladder having the shape of a bead going around the perimeter of the opening of said shell and interposed between said opening and said face of the patient, it is advantageous for:

said flexible envelope to be a sleeve folded back around said bead, said sleeve having a part internal to said shell and a part external to said shell, these parts being connected to each other by an intermediate part bent back around said bead;

said internal part of the flexible envelope to define with the internal wall of said shell an internal space which, for example, communicates with said chamber; and said external part of the flexible envelope to define with the external wall of said shell an external space which, for example, communicates with the outside.

Such a sleeve may either be removably attached to said shell or be integral with the latter. In the latter case, it is advantageous for said sleeve to be integral with the shell at the time of manufacture of the respiratory assistance mask, which may therefore be of the type which can be thrown away after use. On the other hand, in the first case, the sleeve may be attached at any moment to a respiratory mask originally manufactured without a sleeve.

In such a respiratory mask, said internal space may communicate with said chamber by virtue of at least one orifice provided through said internal wall of the sleeve. As regards said external space, this may either be open to the outside or may communicate with the outside by means of at least one orifice provided through said external part of the sleeve.

In the latter case, in order for said flexible envelope to be permanently inflated, it is preferable to ensure that the total flow section of the orifice or orifices provided through said internal part of the sleeve to be greater than the total flow section of the orifice or orifices provided through said external part of said sleeve.

In an alternative embodiment of the respiratory assistance apparatus according to the present invention, in which said apparatus includes a tubular element, the internal volume of which defines said chamber and which is intended to be inserted into a nostril of the patient, said respiratory-gas inlet and outlet being formed by the opposite ends of said tubular element and said inflatable bladder being in the form of an inner balloon supported by the external wall of said tubular element and interposed between the latter and the internal wall of said nostril, said flexible envelope may be in the form of an outer balloon surrounding said inner balloon and supported by said external wall of said tubular element.

Said outer balloon may then communicate, at its distal end, with said chamber via at least one orifice provided through the wall of said tubular element, and, at its proximal end, with the outside via at least one orifice provided through the wall of said outer balloon.

Here again, and for the same reason as mentioned above, the total flow section of the orifice or orifices provided through said wall of the tubular element is advantageously greater than the total flow section of the orifice or orifices provided through the wall of said outer balloon.

BRIEF DESCRIPTION OF THE DRAWINGS

The figures of the apppended drawing will make it clearly understood how the invention may be realized. In these figures, identical references denote similar elements.

FIG. 1 diagrammatically illustrates, in axial cross section, an embodiment of the respiratory assistance apparatus according to the present invention, this being in the form of a mask.

FIG. 2 diagrammatically illustrates, also in axial cross section, an alternative embodiment of the mask of FIG. 1.

DETAILED DESCRIPTION OF THE INVENTION

Figure 3A:
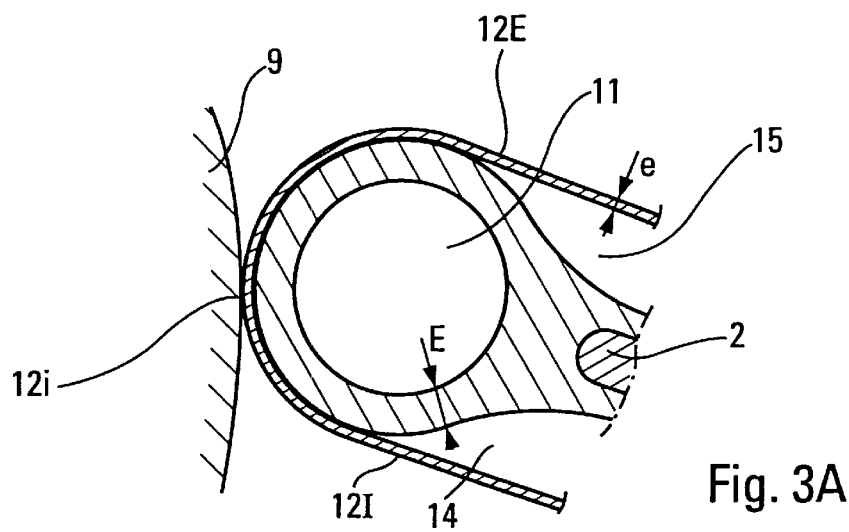
FIGS. 3A and 3B diagrammatically illustrate, in enlarged partial views, the process whereby sealing is obtained with the masks of FIGS. 1 and 2.

The respiratory assistance apparatus 1, according to the present invention and shown in FIG. 1, is in the form of a respiratory mask comprising a hollow rigid shell 2 defining an inner chamber 3. Provided at the bottom of the shell 2 is a respiratory-gas inlet 4, 1for example by means of a tubular endpiece 5, integral with said shell, which can be connected to a respirable-gas source (not shown), for example a pressurized bottle, via a suitable nozzle 6. In FIG. 1, the respirable-gas inflow is portrayed by the arrow 7.

The inner chamber 3 has a respiratory-gas outlet consisting of the opening 8 of said rigid shell 2. The latter is intended to be applied, by its opening 8, to the face 9 of a patient (shown in dot-dash lines) and enclosing the nose 10 of the latter.

In order to ensure gas-tightness between the opening 8 of the shell 2 and the face 9, the respiratory apparatus 1 includes a thin-wall inflatable bladder in the form of a bead 11, integral with the shell 2 and going around the outline of the opening 8 of the latter, said bead 11 being interposed between said opening 8 and the patient's face 9 when the shell 2 is applied against the patient's face 9.

According to the present invention, the respiratory assistance apparatus 1 also includes a flexible envelope 12, the wall thickness e of which is very much less than that E of said bead 11 (see FIGS. 3A, 3B) so that said flexible envelope 12 is much more flexible than the latter. For example, the flexible envelope 12 is made of a plastic film a few microns in thickness.

The flexible envelope 12 surrounds the bead 11 and communicates, on the one hand, with the inner chamber 3 and, on the other hand, with the outside 13. For this purpose, the envelope 12 is in the form of a sleeve, for example a cylindrical or conical sleeve, folded back around the bead 11 and comprises:

- an internal part 12I, which is placed inside the shell 2, in the chamber 3 of the latter, and which defines, with the internal wall 2I of said shell 2, an internal space 14;
- an external part 12E, which is placed outside the shell 2 and which defines, with the external wall 2E of the latter, an external space 15; and
- an intermediate part 12i, bent back around the bead 11 and connecting said internal and external parts 12I and 12E.

In the embodiment shown in FIG. 1, the sleeve 12 is removably attached to the shell 2 and is fastened to the latter, for example, by the internal part 12I being passed through the tubular endpiece 5 and being folded back around the free end of the latter. The sleeve 12 may then be removably attached so that its free end folded back around said tubular endpiece 5 is pinched between the latter and the nozzle 6. In addition, communication between the internal space 14 and the inner chamber 3 is provided by orifices 16 provided through the internal wall 12I of the sleeve 12, whereas the external space 15 is open to the outside 13.

The alternative embodiment 20 of the respiratory assistance apparatus according to the present invention shown in FIG. 2 again has the various elements 2 to 16 described in relation to FIG. 1. However, in the apparatus 20, the sleeve 12 is permanently attached to the shell 2 and, compared with the apparatus 1, this apparatus 20 has the following differences:

- the internal part 12I is welded or adhesively bonded at 21 to the internal wall 2I of the shell 2;
- the external part 12E is welded or adhesively bonded at 22 to the external wall 2E of the shell 2 so that the space 15 is enclosed and so that said external part 12E must include orifices 23 for bringing the space 15 into communication with the outside 13. In this case, it is advantageous for the total flow section of the orifice or orifices 16 to be greater than the total flow section of the orifice or orifices 23.

Figure 3B:
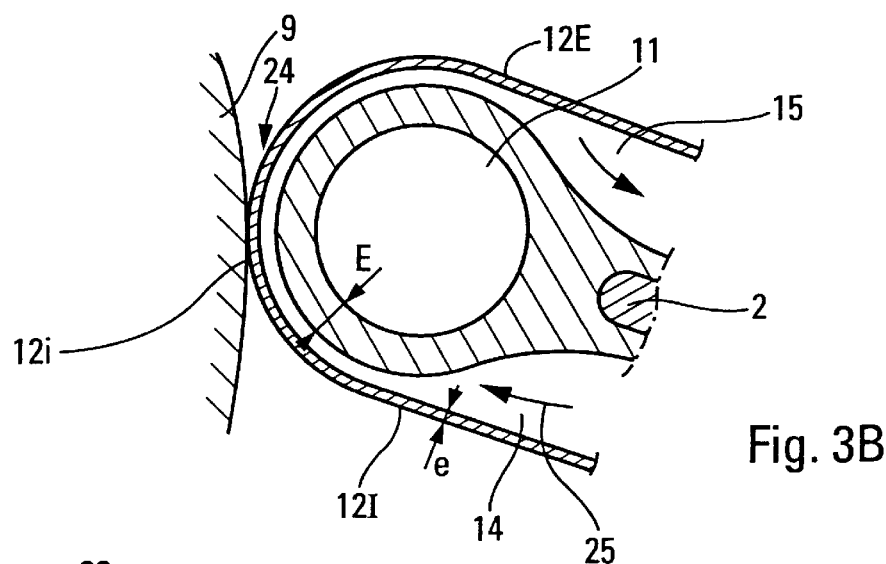

When the respiratory assistance mask 1 or 20 is applied to the face 9 of a patient, the bead 11, because of its relative rigidity and of the irregularities in the contours of this face, cannot be applied uniformly to the latter in a strictly sealed manner. Admittedly, over most of its perimeter, said bead 11 is applied so as to seal against the face 9, as illustrated in FIG. 3A. In this case, the intermediate part 12I of the envelope 12 is itself pressed between the bead 11 and the face 9. On the other hand, in certain places on said bead 11, the latter is held away from the face 9 leaving a space 24 between it and the face 9 (see FIG. 3B).

In the latter case, the respiratory gas penetrating the shell 2 via the opening 4 (arrow 7) and flowing into the internal space 14 through the orifices 16 (arrows 25) inflates the intermediate part 12i of the flexible envelope 12 which is applied so as to seal against the face 9, closing off said space 24. This gas then flows between the bead 11 and the intermediate envelope part 12i and penetrates the external space 15, from where it discharges to the outside 13 (arrows 26) either via the opening of the sleeve 12 (FIG. 1) or through the orifices 23 (FIG. 2).

Thus it may be seen that the envelope 12 allows perfect sealing of the apparatuses 1 and 20 at the places where this sealing cannot be provided by the bead 11.

Figure 4:
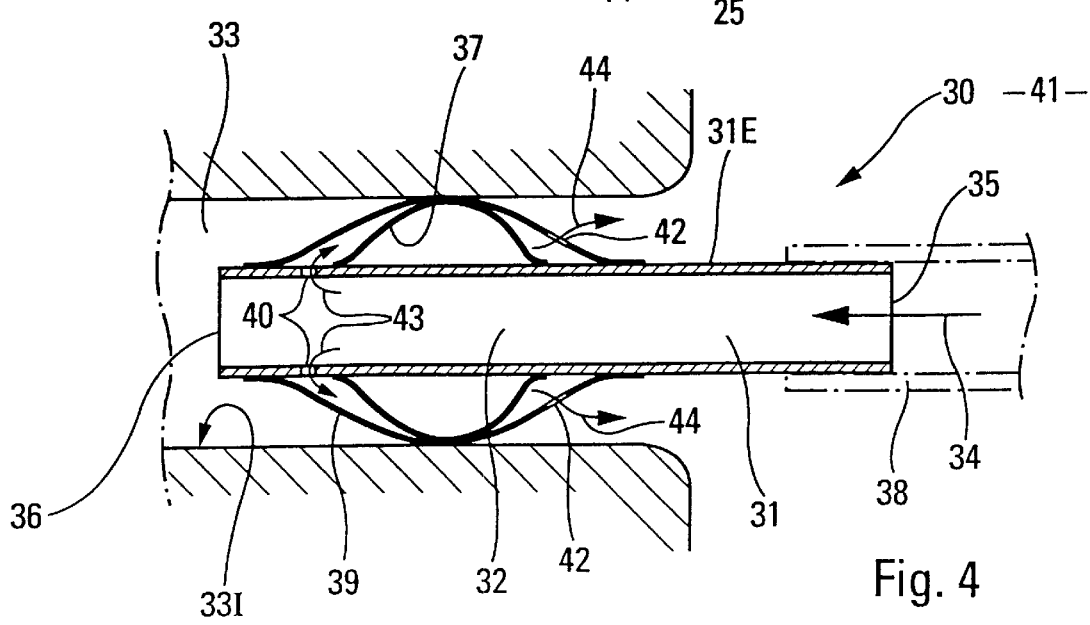
FIG. 4 diagrammatically illustrates, in axial cross section, an alternative embodiment of the respiratory assistance apparatus according to the present invention, this being in the form of a tube.

In the alternative embodiment diagrammatically illustrated in FIG. 4, the respiratory assistance apparatus 30 according to the present invention is in the form of a tubular element 31, the internal volume of which defines a chamber 32 and which is intended to be inserted into a nostril 33 of a patient. Respiratory gas, coming from a source, not shown but portrayed by the arrow 34, is introduced via a nozzle 38 into said tubular element 31 through the proximal end 35 of the latter and is sent to the lungs of said patient through the distal end 36 of said tubular element, which emerges in the nostril 33.

The apparatus 30 comprises, in a known manner, an inflatable holding and sealing bladder 37 in the form of an inner balloon which inflates so as to bear against the internal wall 33I of the nostril 33. The inner balloon 37 is supported by the external wall 31E of the tubular element 31 and is interposed between the latter and said internal wall 33I of the nostril 33.

According to the present invention, the inner balloon 37 is surrounded by an outer balloon 39, supported by said external wall 31E of the tubular element 31, said outer balloon 39 being made of a very thin plastic film.

The outer balloon 39 communicates, at its distal end, with the chamber 32 via orifices 40 provided through the wall of the tubular element 31 between the distal ends of the inner balloon 37 and of the outer balloon 39. At its proximal end, the outer balloon 39 communicates with the outside 41 via orifices 42 provided through the wall of the outer balloon 39.

It will readily be understood that, in a manner similar to that explained above with regard to FIGS. 3A and 3B with regard to the sleeve 12, the outer balloon 39 is able to seal between the outlet 36 of the tubular element 31 and the internal wall 33I of the nostril 33 at the places where the inner balloon 37 is unable to seal.

What is claimed is:

1. A respiratory assistance apparatus making it possible for a respiratory gas coming from an external source to be taken into the lungs of a patient, said apparatus comprising:

a chamber provided with a respiratory-gas inlet intended to be connected to said source and with a respiratory-gas outlet intended to be connected to an airway of said patient;

a thin-wall inflatable flexible bladder intended to bear on a part of said patient in order to seal between said respiratory-gas outlet and the outside; and an inflatable flexible envelope surrounding said inflatable flexible bladder, a wall thickness of said envelope being less than a wall thickness of said inflatable bladder in order to give said envelope a greater flexibility than a flexibility of the inflatable bladder.

2. The respiratory assistance apparatus as claimed in claim 1, wherein said flexible envelope is made of a plastic film a few microns in thickness.

3. The respiratory assistance apparatus as claimed in claim 1, wherein said flexible envelope is inflated using said external respiratory-gas source.

4. The respiratory assistance apparatus as claimed in claim 3, wherein said flexible envelope communicates, on one side of said bladder, with said chamber and on another side of said bladder with the outside.

5. The respiratory assistance apparatus as claimed in claim 1, wherein said apparatus has the shape of a mask, said chamber is bounded by a hollow shell intended to be applied, by an opening thereof which constitutes said gas outlet, to the face of a patient, enclosing the patient's nose, the respiratory-gas inlet being provided in a bottom of said shell and said inflatable bladder having the shape of a bead going around the perimeter of the opening of said shell and interposed between said opening and said face of the patient; said flexible envelope is a sleeve folded back around said bead, said sleeve having a first part internal to said shell and a second-part external to said shell, said first parts and said second part being connected to each other by a third intermediate part bent back around said bead; said first part of the flexible envelope defines with an internal wall of said shell an internal space; and said second part of the flexible envelope defines with an external wall of said shell an external space.

6. The respiratory assistance apparatus as claimed in claim 5, wherein said internal space communicates with said chamber and wherein said external space communicates with the outside.

7. The respiratory assistance apparatus as claimed in claim 5, wherein said sleeve is removably attached to said shell.

8. The respiratory assistance apparatus as claimed in claim 5, wherein said sleeve is fastened to said shell.

9. The respiratory assistance apparatus as claimed in claim 6, wherein said external space is open to the outside.

10. The respiratory assistance apparatus as claimed in claim 6, wherein said external space communicates with the outside by means of at least one orifice provided through said second part of the sleeve.

11. The respiratory assistance apparatus as claimed in claim 1, including a tubular element, the internal volume of which defines said chamber and which is intended to be inserted into a nostril of the patient, said respiratory-gas inlet and outlet being formed by opposite ends of said tubular element and said inflatable bladder being in the form of an inner balloon supported by an external wall of said tubular element and interposed between the tubular element and an internal wall of said nostril, wherein said flexible envelope is in the form of an outer balloon surrounding said inner balloon and supported by said external wall of said tubular element.

12. The respiratory assistance apparatus as claimed in claim 11, wherein said outer balloon communicates, at its distal end, with said chamber via at least one orifice provided through the wall of said outer tubular element, and, at its proximal end, with the outside via at least one orifice provided through a wall of said outer balloon.

\* \* \* \* \*